US007235393B2

(12) United States Patent
Gao et al.

(10) Patent No.: US 7,235,393 B2
(45) Date of Patent: Jun. 26, 2007

(54) METHOD FOR DIRECT RESCUE AND AMPLIFICATION OF INTEGRATED VIRUSES FROM CELLULAR DNA OF TISSUES

(75) Inventors: Guangping Gao, Rosemont, PA (US); James M. Wilson, Gladwyne, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 583 days.

(21) Appl. No.: 10/420,284

(22) Filed: Apr. 22, 2003

(65) Prior Publication Data

US 2003/0207259 A1  Nov. 6, 2003

Related U.S. Application Data

(60) Provisional application No. 60/376,469, filed on Apr. 29, 2002.

(51) Int. Cl.
*C12N 15/864* (2006.01)
*C12N 5/10* (2006.01)
*C12N 7/01* (2006.01)
*C12N 7/02* (2006.01)
*C12N 7/08* (2006.01)
*A61K 48/00* (2006.01)

(52) U.S. Cl. .................. 435/239; 435/320.1; 435/325; 435/366; 435/369; 435/183; 435/235.1; 435/5; 435/6; 435/237

(58) Field of Classification Search ..................... None
See application file for complete search history.

(56) References Cited

U.S. PATENT DOCUMENTS

| 5,773,289 | A | 6/1998 | Samulski et al. |
| 6,086,913 | A | 7/2000 | Tam et al. |
| 6,261,834 | B1 | 7/2001 | Srivastava |
| 6,528,305 | B2* | 3/2003 | Thompson et al. ......... 435/325 |
| 6,815,180 | B1* | 11/2004 | Kim ........................ 435/69.1 |
| 2003/0138772 | A1 | 7/2003 | Gao et al. |

FOREIGN PATENT DOCUMENTS

| EP | 711829 A2 | 5/1996 |
| WO | WO94/12649 A2 | 6/1994 |
| WO | WO96/14408 A2 | 5/1996 |
| WO | WO99/02647 A1 | 1/1999 |
| WO | WO00/75353 A1 | 12/2000 |
| WO | WO03/042397 A2 | 5/2003 |

OTHER PUBLICATIONS

New England Biolabs Catalog, 1996-1997, pp. 2, 18, 19, 21, 28, 31-32, 34 and 43.*

Yang et al, Role of Viral Antigens in Destructive Cellular Immune Responses to Adenovirus Vector-Transduced Cells in Mouse Lungs, J. Virol., 70(10):7209-7212 (Oct. 1996).

K. Fisher et al, Recombinant Adenovirus Deleted of all Viral Genes for Gene Therapy of Cystic Fibrosis, Virology, 217:11-22 (1996).

Yang et al, MHC Class I-Restricted Cytotoxic T Lymphocytes to Viral Antigens Destroy Hepatocytes in Mice Infected with E1-Deleted Recombinant Adenoviruses, Immunity, 1:433-442 (Aug. 1994).

R. Parks et al, A Helper-Dependent System for Adenovirus Vector Production Helps Define a Lower Limit for Efficient DNA Packaging, J. Virol., 74 (4):3293-3298 (Apr. 1997).

M. Morsey et al, An Adenoviral Vector Deleted for all Viral Coding Sequences Results in Enhanced Safety and Extended Expression of a Leptin Transgene, Proc. National Acad. Sci. USA, 95:7866-7871 (Jul. 1998).

R. Parks et al, A Helper-Dependent Adenovirus Vector System: Removal of Helper Virus by Cre-Mediated Excision of the Viral Packaging Signal, Proc. Natl. Acad. Sci. USA, 93:13565-13570 (Nov. 1996).

K. Mitani et al, Rescue, Propagation, and Partial Purification of a Helper Virus-Dependent Adenovirus Vector, Proc Natl. Acad. Sci. USA, 92:3854-3858 (Apr. 1995).

G. Schiedner et al, Genomic DNA Transfer with a High-Capacity Adenovirus Vector Results in Improved in Vivo Gene Expression and Decreased Toxicity, Nature Genetics, 18(2):180 (Feb. 1998).

N. Whittle, Gene Therapy- The Gutless Approach Pays Off, TIG, 14(4):136-137 (Apr. 1998).

Y. Yang et al, Immune Responses To Viral Antigens Versus Transgene Product in the Elimination of Recombinant Adenovirus-Infected Hepatocytes in Vivo, Gene Therapy, 3:137-144 (1996).

Scheiflinger et al, Construction of Chimeric Vaccinia Viruses by Molecular Cloning and Packaging, Proc. Natl. Acad. Sci. USA, vol. 89, pp. 9977-9981, (Nov. 1992).

Hillgenberg et al, System for Efficient Helper-Dependent Minimal Adenovirus Construction and Rescue, Human Gene Therapy, vol. 12, No. 6, pp. 643-657, (Apr. 10, 2001) XP009002050.

Xiao et al, Gene Therapy Vectors based on Adeno-Associated Virus Type 1, Journal of Virology, vol. 73, No. 5, pp. 3994-4003, (May 1999) XP002229851.

Farina et al, Replication-Defective Vector Based on a Chimpanzee Adenovirus, Journal of Virology, vol. 75, No. 23, pp. 11603-11613, (Dec. 2001) XP002957497.

Gao et al, High-Titer Adeno-Associated Viral Vectors from a Rep/Cell Line and Hybrid Shuttle Virus, Human Gene Therapy, vol. 9, No. 16, pp. 2353-2362, (Nov. 1, 1998) XP002108355.

(Continued)

*Primary Examiner*—David Guzo
(74) *Attorney, Agent, or Firm*—Howson & Howson LLP

(57) ABSTRACT

A method for isolating AAV viruses from cellular DNA of non-human primate (NHP) tissues by transfecting the DNA of NHP into 293 cells, rescuing the virus and amplifying it through serial passages in the presence of adenovirus helper functions is provided. Also provided are kits useful for performing this method.

29 Claims, No Drawings

OTHER PUBLICATIONS

Dutheil et al., Presence of Integrated DNA Sequences of Adeno-Associated Virus Type 2 in Four Cell Lines of Human Embryonic Origin. vol. 78, pp. 3039-3043 (Nov. 1997).

Sanmiguel et al, Real-Time PCR as an Analytic Tool in Gene Therapy, Molecular Therapy, vol. 7, No. 5, Abstract 913., S352 (May 2003).

Dong et al, A Specific Value to Evaluate the Quality of Adeno-Associated Viral Vectors, Molecular Therapy, vol. 7, No. 5, Abstract 914., S352, (May 2003).

Hillgenberg et al, System for Efficient Helper-Dependent Minimal Adenovirus Construction and Rescue, Human Gene Therapy, 12:643-657, (Apr. 10, 2001).

* cited by examiner

METHOD FOR DIRECT RESCUE AND AMPLIFICATION OF INTEGRATED VIRUSES FROM CELLULAR DNA OF TISSUES

CROSS-REFERENCE TO RELATED APPLICATIONS

This is a non-provisional of U.S. patent application Ser. No. 60/376,469, filed Apr. 29, 2002.

BACKGROUND OF THE INVENTION

Adeno-associated virus (AAV), a member of the Parvovirus family, is a small nonenveloped, icosahedral virus with single-stranded linear DNA genomes of 4.7 to 6 kb (Mr. $1.5-2.0 \times 10^6$). AAV is assigned to the genus, *Dependovirus*, because the virus was discovered as a contaminant in purified adenovirus stocks. AAV's life cycle includes a latent phase at which AAV genomes, after infection, are site specifically integrated into host chromosomes and a lytic or production phase in which, following either adenovirus or herpes simplex virus super-infection, the integrated genomes are subsequently rescued, replicated, and packaged into infectious viruses. The properties of simple genomic structure, non-pathogenicity, broad host range of infectivity, including non-dividing cells, and potential site-specific chromosomal integration make AAV an attractive tool for gene transfer. Recent studies suggest that AAV vectors may be the preferred vehicle for achieving stable gene expression.

To date, six different serotypes of AAV (AAV1–6) have been isolated from human or non-human primates (NHP), well characterized and vectored for gene transfer applications. All of them have been isolated as infectious viruses from either contaminated adenovirus preparations or tissues specimen of primate and non-human primate origin. Among them, AAV1 and AAV4 were isolated from non-human primates; AAV2, 3 and 5 were derived from humans, and AAV6 was a contaminant of a human adenovirus preparation.

Recently, taking advantage of the AAV's ability to penetrate the nucleus, to integrate into host and establish a latent infection in the absence of a helper virus co-infection, we invented a polymerase chain reaction (PCR)-based strategy for isolation of sequences of novel AAVs from cellular DNAs prepared from different tissues of non-human primate origin. Using this strategy, we have isolated at least 16 molecular types and 8 molecular subtypes of novel AAVs, generated recombinant viruses for two of them to evaluate their performance in gene transfer applications.

There remains a need in the art for reliable methods of identifying and isolating AAV virions from cellular sources.

SUMMARY OF THE INVENTION

The present invention provides a unique approach to isolating novel AAV viruses from cellular DNA of tissues by transfecting the cellular DNA into cells, rescuing the virus and amplifying the virus through serial passages in the presence of adenovirus helper functions. This strategy is a very useful and practical tool for isolating novel AAVs, and other helper-dependent integrated viruses from tissues, particularly non-human primate (NHP) and human tissues.

These and other aspects of the invention will be readily apparent from the following detailed description of the invention. As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

DETAILED DESCRIPTION OF THE INVENTION

In one aspect, the invention provides a method of direct rescue of integrated viral or non-viral sequences from cellular DNA from human or non-human tissues.

The method is particularly well suited for use in rescue of helper-dependent, integrated viruses such an adeno-associated virus (AAV). For example, using a novel AAV serotype recently isolated, the method of the invention was demonstrated to work very well. AAV8 sequences and rep/cap protein expression were dramatically amplified in 293 cells after transfection and serial passages. However, although the examples herein demonstrate the rescue and amplification of a novel AAV serotype, the method of the invention is readily applicable to both known and unknown AAV serotypes, and other viral and non-viral sequences that integrate into the genome of the host cell. Such other viral sequences including retroviruses such as feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumavirinal)], among others. Other suitable uses for the method of the invention will be readily apparent to one of skill in the art.

As used herein, a sample is any source containing nucleic acids, e.g., tissue, tissue culture, cells, cell culture, solid tumors, and biological fluids including, without limitation, urine and blood. These nucleic acid sequences may be DNA or RNA from plasmids, natural DNA or RNA from any source, including bacteria, yeast, viruses, and higher organisms such as plants or animals. In one desirable embodiment, the cells are from a non-human primate or a human source. However, cells from a variety of mammalian and non-mammalian species may also be utilized. The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

Cellular DNA is extracted from extracted from the cellular source using any of a variety of conventional techniques. DNA or RNA is extracted from the sample by a variety of techniques known to those of skill in the art, such as those described by Sambrook, Molecular Cloning: A Laboratory Manual (New York: Cold Spring Harbor Laboratory).

The DNA from the sample is incubated in the presence of a restriction enzyme that is selected to preferentially cleave the genomic DNA native to the host organism without cleaving the target integrated foreign DNA (e.g., AAV).

Typically, the amount of target integrated foreign DNA (e.g., AAV) is small compared to the amount of host DNA in the sample. Thus, this digestion step results in digestion of the host DNA in the cellular sample into multiple fragments, while maintaining the AAV intact. Desirably, the restriction enzyme is selected which contains multiple recognition sites in the host DNA and in any helper vectors used, but only a minimal number of recognition sites in the target AAV genome (or other target integrated DNA). Most desirably, the restriction enzyme selected does not contain any recognition sites in the target integrated DNA. In the present application, such a restriction enzyme is termed a rare cutter. Examples of such rare cutters include those having recognitions sites for seven, eight, or more bases, including, e.g., FseI, PacI, PmeI, PsrI, BcgI, BglI, BsabI, BstXI, DrdI, EcoNI, FseI, MaM I, Msl I, Mwo I, Psha I, Sfi I, Swa I, Xcm I, and Xmn I, and the like. Suitable rare cutters may be identified using information readily available to those of skill in the art in the literature and in a variety of on-line databases, e.g., the REBASE™ database. For example, a suitable rare cutter for use in the method of the invention when the target integrated DNA is AAV serotype 8 includes, e.g., PmeI. Other suitable cutters for the method can be readily determined using a variety of computer programs and/or on-line databases. Suitable restriction enzymes are available from a variety of commercial sources including, e.g., England Biolabs, Obiogene, Lift Technology, Roche, BB Clontech, Stratagene, Amersham Pharmacia, among others.

Once the appropriate sample and digestion enzyme is selected, conventional digestion techniques are utilized. Typically, the sample of DNA mixed with the restriction enzyme is incubated for about 12 to about 48 hours. Following this, a conventional phenol/chloroform extraction step is performed. For example, phenol/chloroform extraction may be utilized, followed by precipitation with ethanol, and dissolving the precipitate (e.g., in TE or another suitable buffer) for use the remainder of the method steps. See, e.g., Sambrook, Molecular Cloning: A Laboratory Manual, $2^{nd}$ Ed., 5.28–5.32, Appendix E.3–E.4 (Cold Spring Harbor Press, Cold Spring Harbor, N.Y., 1989). Other suitable methods may be provided by the manufacturer or vendor of the restriction enzyme utilized, or otherwise known to those of skill in the art.

After the cellular DNA in the sample has been digested, the digested DNA is transfected into a suitable cell using conventional techniques. Suitably, the digested DNA is transfected so as to maximize the concentration of cellular DNA transfected in the cells. For example, this can be an amount of about 0.2 μg to about 2 μg DNA per $5 \times 10^5$ cells with cells at a density of 50% to 80%. However, these amounts may be adjusted as needed or desired, taking into consideration the size of the cell plate, and the cell types, among other considerations.

The host cell itself may be selected from among any biological organism, including prokaryotic (e.g., bacterial) cells, and eukaryotic cells, including, insect cells, yeast cells and mammalian cells. The host cell is capable of infection or transfection of DNA and expression of the transfected DNA. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

Suitably, for isolation and amplification of an AAV, the cell contains, or is provided with, the helper functions necessary for replication of AAV. These helper functions include, at a minimum, the E1a, E1b, E2a, E4, and VAI RNA functions from an adenovirus. See, e.g., WO 99/47691, published Sep. 23, 1999; RM Kotin, *Hu Gene Ther.*, 5:793–801 (1994); WO 99/15685, published Apr. 1, 1999. In addition, helper AAV functions can optionally be supplied and are desirable where low copy numbers of AAV in the sample are suspected.

The helper functions provided by an adenovirus may be supplied by a wild-type adenovirus, and may be of human or non-human origin, preferably non-human primate (NHP) origin. The DNA sequences of a number of human adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, "Adenoviridae and Their Replication", in VIROLOGY, 2d ed., pp. 1679–1721 (1990)]. Similarly adenoviruses known to infect non-human primates (e.g., chimpanzees, rhesus, macaque, and other simian species) or other non-human mammals may also be employed in the vector constructs of this invention. For example, suitable adenoviruses are available from the ATCC and include, without limitation, chimpanzee adenoviruses Pan 5 [VR-591], Pan6 [VR-592], Pan7 [VR-593], and C1 and C68 (Pan9), described in U.S. Pat. No. 6,083,716; and simian adenoviruses including, without limitation SV1 [VR-195]; SV25 [SV-201]; SV35; SV15; SV-34; SV-36; SV-37, and baboon adenovirus [VR-275], among others. In addition to wild-type adenoviruses, recombinant viruses or non-viral vectors (e.g., infectious and non-infectious plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. In the following examples, an adenovirus type 5 (Ad5), Pan6, and Pan9 are used for convenience. However, one of skill in the art will understand that comparable regions derived from other adenoviral strains may be readily selected and used in the present invention in the place of (or in combination with) these serotypes.

In one embodiment, the cell contains only the adenovirus E1, E2a and/or E4 ORF6 in order to avoid homologous recombination of a contaminating virus during passaging to amplify the AAV. In another embodiment, the cell stably expresses the adenoviral E1a and E1b gene functions and is provided with the other necessary adenoviral helper functions in trans. An example of a suitable cell is a 293 cell, which is from a cell line available from the American Type Culture Collection [ATCC], Manassas, Va. 20110-2209. Other suitable cells lines are available from the ATCC, commercial sources, or have been described in the literature.

Where AAV helper functions are supplied, e.g., where low copy numbers of AAV in the sample are suspected, the host cell can optionally stably contain or can otherwise be provided with AAV helper functions. In one embodiment, the AAV helper functions are rep functions which are present in the absence of cap. In this embodiment, the rep functions may be supplied by a single AAV serotype. Alternatively, rep functions from two, three or more different AAV serotypes may be selected. Suitably, the rep functions may be selected from among any desired AAV serotype.

Suitable AAV serotypes include, AAV1, AAV2, AAV3, AAV4, AAV5, or AAV6, which have been described in the literature, AAV serotypes such as AAV8, which is the subject of International Patent Application No. PCT/US02/33630, filed Nov. 12, 2002; AAV9 that is the subject of International Patent Application No. PCT/US02/33631; and AAV7, AAV10, AAV11, AAV12, and others that are identified in co-pending U.S. patent application Ser. No. 10/291,583, which are incorporated by reference herein. Additionally, the sequences of AAV7 and AAV8 have been described [G–P. Gao, et al, *Proc Natl Acad. Sci USA*, 99(18):11854–11859 (Sep. 3, 2002); GenBank database accession no. AF513851 (AAV7) and accession number AF513852 (AAV8). A variety of AAV serotypes may be isolated according to procedures described in these co-pending applications, or obtained from a variety of sources, including the American Type Culture Collection (ATCC), Manassas Va. Sequences for these AAV serotypes have been published and many are available from databases such as PubMed and GenBank.

In another embodiment, both rep and cap are utilized as the AAV helper functions. In this embodiment, the rep functions and the cap functions may be supplied by the same AAV serotype or from different AAV serotypes. Where desired, the rep functions and/or the cap functions may be supplied by two, three or more different AAV serotypes, in which the sources of AAV for the rep are the same or different from the sources of AAV serotypes for the cap. Suitably, the rep and cap functions may be selected from among any desired AAV serotype.

One host cell useful in the present invention is a host cell stably transformed with the sequences encoding rep and cap, and which is transfected with the adenovirus E1, E2a, and E4ORF6 DNA. Stable rep and/or cap expressing cell lines, such as B-50 (PCT/US98/19463)now WO 99/15685, or those described in U.S. Pat. No. 5,658,785, may also be similarly employed. Another desirable host cell contains the minimum adenoviral DNA which is sufficient to express E4 ORF6. Yet other cell lines can be constructed using the other AAV rep and/or cap sequences. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Optionally, the desired AAV helper functions, e.g., rep and/or cap are provided to the host cell by one or more vectors carrying the sequences encoding the desired helper functions. See, e.g., U.S. Pat. No. 6,203,975 [plasmid carrying rep/cap proteins optionally conjugated to a recombinant adenovirus] and U.S. Pat. No. 6,258,595 [describing a number of plasmids carrying rep and/or cap functions.] The rep and cap sequences, along with their expression control sequences, may be supplied on a single vector, or each sequence may be supplied on its own vector. Preferably, the rep and cap sequences are supplied on the same vector. Alternatively, the rep and cap sequences may be supplied on a vector that contains other DNA sequences that are to be introduced into the host cells, e.g., the helper adenoviral functions. Preferably, the promoter from which the rep or cap proteins are expressed may be any of the constitutive, inducible or native promoters known to one of skill in the art or as discussed above. In one embodiment, an AAV P5 promoter sequence is employed for expression of the rep proteins. While it may be obtained from any AAV source, the parvovirus P5 promoter is preferably of the same serotype as the serotype that provides the rep and cap gene sequences. Alternatively, the promoter may be a P5 promoter from another AAV type than that which provides the rep and cap sequences. AAVs known to infect other humans or other animals may also provide the P5 promoter. The selection of the AAV to provide any of these sequences does not limit the invention. In another embodiment, the promoter for rep is an inducible promoter. As discussed above, inducible promoters include, without limitation, the metallothionine (MT) promoter; the dexamethasone (Dex)-inducible mouse mammary tumor virus (MMTV) promoter; the T7 polymerase promoter system; the ecdysone insect promoter; the tetracycline-repressible system; the tetracycline-inducible system; the RU486-inducible system; and the rapamycin-inducible system. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

Exemplary molecules providing the AAV rep and cap proteins are plasmids, e.g., pMT-Rep/Cap, pP5-Rep/Cap and pMMTV-Rep/Cap. These plasmids contain a neomycin selective marker gene and express the AAV rep/cap genes driven by either their native P5 promoter (pP5-Rep/Cap), the zinc-inducible sheep metallothionine promoter (pMTRep/Cap), or the dexamethasone (Dex)-inducible mouse mammary tumor virus (MMTV) promoter (pMMTV-Rep/Cap). Although these proteins may be provided to the cell by various means, exemplary methods of the invention include use of various plasmids. For construction of plasmid pMT-Rep/Cap, the ORF6 sequence was removed from a pMTE4ORF6 plasmid [G. P. Gao et al, *J. Virol.*, 70:8934–8943 (1996)] by BamHI digestion and replaced with a 4.1 kb rep/cap fragment that was prepared by PCR amplification using pSub201 plasmid [R J Samulski, et al., *J. Virol.*, 63:3822–3828 (1989)] as a template. Plasmid pMMTV-Rep/Cap was constructed in the same way as pMT-Rep/Cap, except that a pMMTVE4ORF6 plasmid [Gao et al, cited above] was used as the vector backbone. For construction of P5-Rep/Cap, the MT promoter and ORF6 sequences were removed from a pMTE4ORF6 plasmid [G. P. Gao et al, *J. Virol.*, 70:8934–8943 (1996)] by EcoRI/BamHI digestion and replaced with a 4.3 kb P5-Rep/Cap fragment which was isolated from a pSub201 plasmid [R J Samulski, et al, *J. Virol.*, 63:3822–3828 (1989)] by XbaI digestion. Plasmid construction involved conventional genetic engineering methods, such as those described in Sambrook et al, cited above. All of the above-cited references are incorporated by reference herein.

A variety of other plasmid constructs providing the rep and/or cap proteins are known in the art and may be employed in the host cell of the invention. For example, the rep and/or cap constructs may omit the spacer between the promoter and the rep and/or cap genes referred to in the construct described above. Other constructs of the art, such as that described in U.S. Pat. No. 5,622,856, which places the P5 promoter 3' to the rep/cap genes, may also be employed in this context.

The molecule providing the rep and/or cap proteins may be in any form that transfers these components to the host cell. In one embodiment, this molecule is in the form of a plasmid, which may contain other non-viral sequences, such as those for marker genes. Suitably, this molecule does not contain the AAV ITRs and generally does not contain the AAV packaging sequences. Thus, a variety of vectors are known for delivering AAV helper functions to a host cell. However, selection of an appropriate vector for delivery of AAV helper functions is not a limitation of the present invention.

According to the present invention, any desired helper functions (e.g., adenovirus, AAV rep, AAV cap, or other helper functions) that are not stably contained in the cell are provided to the cell by a suitable vector. As used herein, a vector is any genetic element that can be delivered to a host cell, e.g., naked DNA, a plasmid (infectious or non-infectious), phage, episome, transposon, cosmid, virus, etc. that transfer the sequences carried thereon. The selected vector may be delivered to the cells by any suitable method, including transfection, electroporation, liposome delivery, membrane fusion techniques, high velocity DNA-coated pellets, infection and protoplast fusion. Transfection is referred to throughout this specification for purposes of convenience only, is not a limitation on the method of transferring the genetic element to the cell.

Thus, unless all necessary helper functions are stably contained in the host cell, the helper functions are supplied by co-transfection, infection or superinfection, as described herein. Suitably, the cells are co-transfected/infected with the helper in an amount of about 0.2 µg to about 2 µg DNA per 1 to $5 \times 10^5$ cells, and more preferably about 1 µg to about 1.8 µg DNA per $5 \times 10^5$ cells. The invention is not limited to this concentration of cells, which may be varied (e.g., from $10^3$ or fewer cells to $10^{12}$ or more cells) depending upon the well plate, cell type, or other factors known to those of skill in the art. The restriction enzyme-digested DNA and the helper vector are suitably provided to the cell at a ratio of 1:1 to 1:10 digested DNA:helper. Alternatively, a higher amount of digested DNA may be provided to the cell than helper vector.

Thus, according to the method of the invention, digested DNA are transfected into host cells for rescue and amplification of the target sequences. In one example, the method of the invention is utilized to rescue an AAV from a primate (human or non-human) tissue.

In one embodiment, the digested DNA is transfected overnight into host cells; the cells are incubated overnight and then superinfected with a helper adenovirus; harvested following full cytopathic effect (CPE) and optionally further passaged. As used herein, superinfection refers to delivery of a helper virus providing any necessary helper functions not provided by the host cell. For example, when the helper functions are provided by an adenovirus, AAV packaging and replication requires, at a minimum, E1 functions (i.e., E1a and E1b), E2a, E4 (or a functional fragment thereof, such as the ORF6 fragment) and VAI RNA. If the host cell does not provide E1 functions, a helper vector, e.g., the helper adenovirus, supplies these functions. Preferably, the E1 functions are stably contained in the host cell.

Thus, following transfection of the selected host cell, the cells are thereafter cultured for the selected host cell in order to permit expression of the helper functions and replication of AAV. Typically, the cells are cultured under conventional conditions for about 18 to about 30 hours, or for convenience, about 24 hours, at which time they are superinfected with an adenoviral helper virus.

For superinfection, a viral vector providing wild-type adenoviral gene functions can be utilized or a recombinant adenoviral genome providing E1 adenoviral functions is provided. Alternatively, when the cell line provides E1 gene functions, a viral vector containing all adenoviral gene functions with the exception of E1 can be utilized. Suitably, however, the host cell is provided with at a minimum, E1a, E1b, E2a, and VAI RNA functions. The adenoviral helper functions may be from the same adenovirus serotype as provides the other helper functions in the cell, or from a transcomplementing serotype. For example, one may utilize a cell line expressing human Ad5 E1a and E1b and a helper virus carrying human or simian adenovirus helper functions (e.g., chimpanzee C68). Alternatively, one may utilize a cell line expressing human Ad5 E1a and E1b, a first helper vector carrying adenovirus helper functions, and an adenovirus for the superinfection step. Many other combinations are possible, and will be readily apparent to one of skill in the art. Suitably, the helper virus is provided at a multiplicity of infection (MOI) in the range of 2 to 5. However, other suitable MOI may be readily determined by one of skill in the art.

Any desired helper AAV functions may be supplied at either time of transfection of the digested DNA or at the time of superinfection. The cells are typically harvested after full CPE is observed, which usually is about 72 to about 96 hours following superinfection. The cells are harvested using conventional techniques. Typically, the culture is subjected to one or preferably several rounds of freeze/thaw, and the resulting crude lysate collected for the next passage or detection of target DNA.

Optionally, the pellet, which contains the total cellular DNA and proteins from the first passage, is subjected to further passaging by repeating the culturing and collection steps. Optionally, a suitable vector may provide additional AAV helper functions during one or more of the additional passaging steps. These steps may be repeated as needed, e.g., for a total of two to fifty passages. However, the passaging steps may be fewer, e.g., for a total of two to thirty passages, two to twenty passages, two to ten passages, two to five passages, or more, where desired.

In a second embodiment, the digested DNA is co-transfected into a host cell which expresses adenoviral E1 functions with an adenoviral helper plasmid which provides only the minimal adenoviral E2a, E4 (or a functional fragment thereof) and VAI RNA functions; harvesting; and superinfecting with virus at the first passage. Alternatively, the host cell does not provide E1 functions and these functions are supplied on a helper vector which may be same or different from that providing the other helper functions. Any desired helper AAV functions may be supplied at either time of transfection of the digested DNA or at the time of superinfection.

In this second embodiment, no CPE is observed, and the cells are typically harvested after about 72 to about 96 hours post-transfection using conventional techniques. Typically, the culture is subjected to freeze-thaw as described above and crude lysate is collected for passaging. At this time, it is necessary to supply adenoviral helper function, preferably in the form of infectious plasmid or virus. Thereafter, the culture is passaged as described in the first embodiment above. In addition, the cell line may optionally be provided with any desired AAV functions by co-transfection or infection at the time of initial transfection with the digested DNA, or preferably, at the time of beginning the first passage (i.e., with superinfection). Optionally, additional AAV helper functions (e.g., rep) may be supplied during one or more of the additional passages.

In yet a third embodiment, the digested DNA is co-transfected into the host cell with an infectious plasmid. Typically, an infectious plasmid contains the full-length adenovirus genome. However, when transfected into a cell line expressing E1 functions, an infectiously plasmid may contain the full-length adenoviral genome with the exception that E1 is deleted or rendered non-functional. Optionally, the cell is also transfected with any desired AAV helper functions. The cells are cultured after CPE is observed using conventional techniques. Typically, the culture is subjected to freeze-thaw, as described above, and the crude lysate is collected for the next passage or detection of target DNA.

Regardless of which of the above three alternative embodiments is utilized, the crude lysate which contains the total cellular DNA and proteins from the first passage is optionally subjected to further passaging by repeating the transfection, culturing and collection steps. These steps may be repeated as needed, e.g., for a total of two to fifty passages. However, the passaging steps may be fewer, e.g., for a total of two to thirty, two to twenty, two to ten, two to five, or more, where desired.

Following collection of the cell pellet from the final passaging step performed, the cellular DNA and proteins in the pellet are assayed to detect the presence of the target integrated DNA, e.g., AAV. This detection step may be performed using any suitable method. In one embodiment, TaqMan PCR techniques are utilized. See, generally, Sambrook et al, cited herein. In another alternative, infectious AAV may be isolated using genome walking technology (Siebert et al., 1995, *Nucleic Acid Research*, 23:1087–1088, Friezner-Degen et al., 1986, *J. Biol. Chem.* 261:6972–6985, BD Biosciences Clontech, Palo Alto, Calif.). In another embodiment, a novel detection method developed in the inventors' laboratory can be utilized. This method is particularly well suited to the detection of AAV of novel and/or unknown serotype and is the subject of a co-pending application, U.S. patent application Ser. No. 10/291,583, filed Nov. 12, 2001, entitled "A Method of Detecting and/or Identifying Adeno-Associated Virus (AAV) Sequences and Isolating Novel Sequences Identified Thereby", which is incorporated by reference herein.

Alternatively, following passaging, the cell pellets are harvested for purification of AAV virion following standard procedures. Among such standard procedures is cesium chloride (CsCl) gradient purification, column chromatography, and techniques such as those described [Gao et al, *Hu Gene Therapy*, 11:2079–2091 (October 2002)] and elsewhere in the literature.

For example, the cells together with transfection medium may be harvested by scrapers and subjected to three rounds of freezing-thawing in ethanol-dry ice and 37° C. water bath. The cells may be centrifuged, e.g., for 15 minutes at 4° C. See, generally, Sambrook et al, cited herein.

Thus, the method of the invention permits detection, identification, and isolation of target viral sequences, particularly integrated viral sequences. The invention further provides novel viruses identified and isolated using the method of the invention. Once so isolated and identified, the novel viruses may be characterized using methods known to those of skill in the art and utilized for a variety of purposes which will be readily apparent to one of skill in the art.

The methods of the invention are particularly well suited for use in detection, identification and isolation of AAV sequences, which may include novel AAV serotypes. The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown integrated target, e.g., an adeno-associated virus (AAV), in a sample. Such a kit may contain vials containing the rare restriction enzyme, cells for passaging the extracted DNA, helper viral plasmids and/or viruses, among other materials.

The invention further provides a kit useful for identifying an AAV serotype detected according to the method of the invention and/or for distinguishing novel AAV from known AAV. In addition, kits of the invention may include, instructions, a negative and/or positive control, containers, diluents and buffers for the sample, indicator charts for signature comparisons, disposable gloves, decontamination instructions, applicator sticks or containers, and sample preparatory cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

The following examples illustrate several aspects and embodiments of the invention.

EXAMPLE 1

Detection and Quantification of AAV8 Sequence in Rhesus Monkey Tissues.

A set of primers and probe were designed based on a stretch of sequence located within the hyper-variable region 4 of the AAV8 capsid gene for real time PCR analysis (TaqMan). The TaqMan analysis was performed for over 110 DNA samples from 10 tissues each of 11 rhesus monkeys of two different colonies. It was found that heart and liver tissues of one monkey (98E056) were most enriched in AAV8 sequence. The genome copies of AAV8 sequence per 1 μg of DNA are 88000 for the heart and 22000 for the liver. With such abundance of AAV8 sequence in these two DNA samples, these were thought to be good candidates for rescue of AAV8 virus.

EXAMPLE 2

Restriction Enzyme Digestion of Tissue DNA

In order to rescue AAV8 from monkey tissue DNAs, delivery of the DNA into appropriate cells is the first step. Direct transfection of high molecular weight cellular DNA into mammalian cells usually results in poor gene transfer efficiency. To overcome this barrier, 5 μgs of liver DNA of monkey #98E056 was treated with Pme I, a non-cutter in the AAV8 genome overnight and then phenol/chloroform extracted, ethanol precipitated and dissolved in TE (1 M Tris, pH 8.0, 0.5 M EDTA, pH 8.0, $dH_20$).

EXAMPLE 3

Transfection and Rescue of AAV8 in 293 Cells

In this study, 293 cells, a human embryonic kidney fibroblast cell line that was transformed by E1 genes of human adenovirus serotype 5, was selected as host for rescue because of its high transfectability and successful applications in producing a variety of AAV vectors of different serotypes. Calcium phosphate method, a method that was commonly used in triple transfection of 293 cells for production of recombinant AAVs of different serotypes, was the method of transfection in this experiment.

The other crucial requirement for rescue of AAV genomes is the presence of appropriate adenovirus helper functions. In this experiment, we selected human adenovirus serotype 5 as the helper to start with based on two observations. The first was that the use of Ad5 helper plasmid in triple transfection of 293 cells resulted in high yield production of AAV2/8 vectors, suggesting that Ad5 is a good helper. The second observation was that monkey 98E056 in whom high copy numbers of AAV8 sequence were detected in liver and heart was treated with a recombinant adenovirus vector through hepatic vein administration before it was sacrificed. This could lead to a speculation that infection of adenvirus resulted in rescue and amplification of AAV8 genomes in some tissues of this monkey.

The 293 cells were seeded in 12 well plates at a density of $5 \times 10^5$ cells per well. The transfection and rescue experiment was carried out as follows.

Group A-1: 1 µg of Pme I treated liver DNA+1 µg of pBluescript DNA (carrier DNA)

Group A-2: 0.2 µg of Pme I treated liver DNA+1.8 µg of pBluescript DNA (carrier DNA)

Group B-1: 1 µg of Pme I treated liver DNA+1 µg of pAdΔF6 DNA (Non-infectious Ad helper plasmid)

Group B-2: 0.2 µg of Pme I treated liver DNA+1.8 µg of pAdΔF6 DNA (Non-infectious Ad helper plasmid)

Group C-1: 1 µg of Pme I treated liver DNA+1 µg of pAdCMVLacZ (infectious Ad plasmid)

Group C-2: 0.2 µg of Pme I treated liver DNA+1.8 µg of pAdCMVLacZ (infectious Ad plasmid)

At 24 hours post transfection, cells in A-1 and A-2 were infected with Ad5 wt virus at a MOI of 2. Cells in A-1, A-2, B-1 and B-2 were harvested at 96 hours post transfection and lysed by 3 cycles of freeze/thaw. Cells in C-1 and C-2 were harvested for crude lysate preparation after full cytopathatic effect (CPE) and observed at day 15 post transfection.

The entire crude cell lysate from each group was then passed onto a 100 mm plate of 293 cells. For group B-1 and B-2, the cells were also superinfected with E1-deleted Ad5 wt virus at a MOI of 5. As a control, a 100 mm plate of 293 cells was infected with the same Ad5 wt virus at a MOI of 5. When full CPE was observed, each infection was harvested. One tenth of each infection was saved for three cycles of freeze/thaw and passed onto another 100 mm plates of 293 cells for the next passage. The remaining infection was spun down to collect the cell pellet for preparation of total cellular DNA and proteins. The process was repeated for each sample for passages 2 and 3 for initial characterizations.

EXAMPLE 4

Characterization of Total DNA, Protein and Crude Lysate of Re-Infected 293 Cells at Different Passages A. TaqMan PCR.

To examine whether AAV8 sequence was rescued and amplified during the serial passages, total DNA extracted from different passages of each experimental group was subjected to TaqMan analysis for AAV8 cap gene sequence. The results are summarized below (GC=genome copy). See Table 1.

TABLE 1

| Samples | AAV8 GC/cell |
|---|---|
| A-1-P1 | $2.7 \times 10^3$ |
| A-1-P2 | $1.1 \times 10^4$ |
| A-1-P3 | $1.7 \times 10^4$ |
| A-2-P1 | 41 |
| A-2-P2 | 15 |
| A-2-P3 | 11 |
| B-1-P1 | $1 \times 10^4$ |
| B-1-P2 | $1.3 \times 10^4$ |
| B-1-P3 | $9.3 \times 10^3$ |
| B-2-P1 | $1.1 \times 10^4$ |
| B-2-P2 | $1.4 \times 10^4$ |
| B-2-P3 | $8 \times 10^3$ |
| C-1-P1 | $1.4 \times 10^4$ |
| C-1-P2 | $1.5 \times 10^4$ |
| C-1-P3 | $1.4 \times 10^4$ |
| C-2-P1 | 6 |
| C-2-P2 | 13 |
| C-2-P3 | 17 |
| Ad-control-P1 | 5 |
| Ad-control-P2 | 17 |
| Ad-control-P3 | 25 |
| 293 cells | 13 |

The data suggested the following:

AAV8 virus was rescued in the transfection process and further amplified during serial passages in A-1, B-1 and B-2 and C-1 groups. Such amplification is not dramatic during the passages, probably due to the limited packaging capacity of AAV in 293 cells and competitive growth inhibitions between Adenovirus and AAV.

When 0.2 µg monkey DNA was used in A-2 and C-2, there was no significant AAV8 sequence detected in any passages. This may imply that a thresh hold of initial genome copy of AAV is required to overcome adenovirus inhibition for rescue and amplification in 293 cells. But in the case of B-2, since both AAV8 and Adenovirus rescues occurred simultaneously, inhibition of AAV8 rescue, replication and packaging by adenovirus replication and packaging is less detrimental, leading to success rescue and amplification of AAV8 even at lower genome copies.

This suggests that how and when adenovirus helper functions are provided are important for rescue and amplification of AAV by this method.

B. PCR Cloning

The TaqMan data suggested some cross reactivity between AAV8 probe/primers and DNA sequences of 293 cells. To confirm the presence of AAV sequence in the infections, two additional tests were carried out.

1. Conventional PCR Amplification of the AAV Signature Region Using the Universal Primer Set.

Crude lysates of A-1-P3, C-1-P3 and Ad-control-P3 were treated with DNase I for 1 hour at 37° C. to digest unpackaged AAV8 genomes. 0.4 µl each of treated lysate was used for 50 μl PCR amplification. The PCR products were examined by 2% agarose gel electrophoresis. The results revealed expected 250 bp signature PCR products in A-1-P3 and C-1-P3 samples, whereas Ad-control-P3 showed no band at all. This confirmed that the signals picked up by TaqMan in A-1 and C-1 were AAV sequence.

2. PCR Cloning and Sequencing to Identify Specific AAV Sequences.

To identify what molecular type(s) of AAV sequences was rescued and packaged in this experiment, a pair of universal set of primers was designed to amplify a 3.1 kb sequence spanning entire cap gene and 3' end of the rep gene. The PCR product is cloned and partially sequenced for identification.

C. Western Blots.

As another way to confirm for the presence of AAV virus in the crude lysate, AAV Rep and Cap protein expression at different passages was examined. In a previous experiment, it was found that Clone B1, a mouse monoclonal antibody to AAV2 capsid proteins, could cross-react with the capsid proteins from AAV1, 5, 7 and 8 well. Extensive sequence comparison of all types of AAVs revealed a strong similarity in the Rep region. It was decided to use Clone 259.5, a mouse monoclonal antibody to AAV2 Rep protein, for the Western blot analysis.

Total cellular proteins were extracted from cell pellets of the passage 3 of some infections and quantified. Five μgs each of total protein was used for the Western blot analysis. The results are summarized in Table 2 below.

TABLE 2

| Samples | Rep | Cap |
| --- | --- | --- |
| A-1-P3 | + + + + | + + + + |
| A-2-P3 | − | − |
| B-1-P3 | + + + + | + + + + |
| B-2-P3 | + + + + | + + + + |
| C-1-P3 | + + + + | + + + + |
| C-2-P3 | − | − |
| Ad-Control-P3 | − | − |
| 293 cells | − | − |
| AAV2/8AlbAlAT virions (1 × 10^10 GC) | − | + + + + |

The data suggested a correlation between genome copies of AAV8 sequence and Rep/Cap expression, indicating the AAV8 sequence presented in the cells was transcriptionally and translationally active.

EXAMPLE 5

Expansion of AAV8 Virions

TaqMan analysis, PCR/cloning and Western blot analysis documented presence of AAV sequence and rep/cap gene expression as described herein.

Using TaqMan technology, it has been determined that two tissues in monkey #98E056 are most enriched in AAV8 sequence. They are heart and liver (88,000 and 22,000 GC of AAV8 per μg of DNA respectively). To study whether the AAV8 sequence in tissue DNA is rescuable and packagable into virions, liver DNA of this monkey was restricted with Pme I, a noncutter in the AAV8 genome and transfected into 293 cells either with infectious or noninfectious adenovirus helper plasmids or followed by adenovirus infection 24 hour later. Crude lysate from each transfection or transfection/infection was harvested at 72 hours post transfection and subjected to serial passages.

More particularly, cellular DNA prepared from monkey liver were restricted with Pme I endonuclease and co-transfected with infectious and non-infectious adenovirus plasmids or control plasmid into 293 cells using conventional calcium phosphate methodology (rhesus monkey liver DNA). A control plasmid was used for mock transfection (pBluescript). Non-infectious adenovirus helper plasmid provided E2a, E4 and VARNA helper functions. An infectious E1-deleted recombinant adenovirus plasmid was used to infect in 293 cells (pAdΔF6). For A-1 and A-2 groups, helper adenovirus was added at 24 hours post-transfection and the cell lysate was harvested 48 hours later for passages (pAdCMVLacZ). For C-1, C-2 and control group, cell lysate was prepared at 72 hours post transfection and the helper virus was added to the 293 cells in the first passage (Ad5 wt virus). See, Table 3.

TABLE 3

AAV8 virus rescue experiment

| | Experimental Groups | | | | | | |
| --- | --- | --- | --- | --- | --- | --- | --- |
| DNA/virus | A-1 | A-2 | B-1 | B-2 | C-1 | C-2 | Control |
| Rhesus Monkey Liver DNA (98E056) | 1 μg | 0.2 μg | 1 μg | 0.2 μg | 1 μg | 0.2 μg | — |
| pBluescript | 1μg | 1.8 μg | — | — | — | — | 2 μg |
| pAdΔF6 | — | — | — | — | 1 μg | 1.8 μg | — |
| pAdCMVLacZ | — | — | 1 μg | 1.8 μg | — | — | — |
| Ad5Wt virus (MOI) | 2 | 2 | — | — | 5 | 5 | 5 |

As a way to confirm for the presence of AAV virus in the crude lysate, AAV Rep and Cap protein expression at different passages was examined. In a previous experiment, it was found that Clone B1, a mouse monoclonal antibody to AAV2 capsid proteins, could cross-react with the capsid proteins from AAV1, 5, 7 and 8 well (data not shown). Extensive sequence comparison of all types of AAVs also revealed a strong similarity in the Rep region.

A mouse monoclonal antibody to AAV2 Rep protein (Clone 259.5) was selected for use in Western blot analysis. Total cellular proteins were extracted from cell pellets of passage 1 of experiments B-1 and B-2 and quantified. Two μgs each of total protein was used for the Western blot analysis of rep and cap. Presence of AAV8 cap gene sequences in the cellular DNA extracted from passage 1 of B-1 and B-2 group was also quantified by TaqMan using AAV8 cap specific primers and probe.

To determine that the AAV genome rescued was indeed AAV8, PCR amplification and cloning of 3.1 kb cap region from DNase I treated crude lysates of passage 3 of C-1 and mock transfection were carried out. As expected, there was no PCR band detected in the mock transfected sample but sequence analysis of C-1 clones confirmed the genomes that were rescued and packaged in 293 cells in the presence of adenovirus helper are AAV8 (data not shown).

The next step is to isolate AAV virions of this molecular entity. As described further in Example 6, the crude lysate of A-1, B-1, C-1 and Ad-control were continuously passed on to 1, 5, and 50 of 150 mm plates of 293 cells. The cell pellets were harvested at 42 hours post infection for CsCl gradient purification of AAV virion following standard procedures.

EXAMPLE 6

Transmission Electron Microscopy Examination of AAV8 Virions and Generation of Infectious Clones Once AAV virions are isolated, transmission electron microscopy examinations of negatively stained samples are performed to demonstrate the morphology of AAV virions. In addition, infectious molecular clones of AAV genomes packaged in the virions are created for further characterization, following the procedure described in Xiao et al., *J. Virol.*, 73(5):3994–4003 (May 1999).

To examine physical virions of AAV8, crude lysate of serial passage of group C-1 together with that of mock transfection group were expanded to 50 plate infections and subjected to CsCl gradient centrifugation for purification of AAV virions. Genome copy concentration of AAV8 was determined by TaqMan analysis. Transmission electron microscopy examination of negatively stained samples was performed. In the results (not shown) C-1 sample illustrated typical AAV virions but Mock transfection had no visible AAV structures.

EXAMPLE 7

Rescue of Novel AAV Identified in Spleen Tissue

Using the methods described herein (see, example 3), an experiment was performed to rescue novel simian AAV identified in spleen tissue of a rhesus monkey. The cellular DNA was treated with PmeI and co-transfected in equal amounts (1 µg each) with an E1-deleted molecular clone of simian adenovirus Pan 6, an E1-deleted molecular clone of simian adenovirus Pan9, and an E1-deleted molecular clone of human Ad5 in 293 cells. The AAV titers were determined by TaqMan analysis at passage 1 post-transfection as described in these examples.

| Helper | AAV titer (TaqMan, universal probe, GC/100 ng DNA) |
|---|---|
| Pan 6 | $1.1 \times 10^8$ |
| Pan 9 | $1 \times 10^6$ |
| Ad 5 | $7.2 \times 10^3$ |

This data suggests that simian adenovirus serotypes can be more efficient in rescue of simian AAV serotypes.

All publications cited in this specification are incorporated herein by reference. While the invention has been described with reference to a particularly preferred embodiments, it will be appreciated that modifications can be made without departing from the spirit of the invention. Such modifications are intended to fall within the scope of the claims.

What is claimed is:

1. A method of direct rescue of adeno-associated viruses (AAV) from cellular DNA from tissues comprising the steps of:
   (a) digesting DNA in a sample of genomic DNA from a mammalian tissue source with a restriction enzyme that cleaves the genomic DNA native to the mammalian tissue source without cleaving AAV genomic DNA;
   (b) transfecting the digested DNA into cells;
   (c) culturing the transfected cells under conditions in which at least the minimal adenoviral functions necessary for packaging and replication of the AAV are expressed in the cells;
   (d) passaging lysate obtained from the culturing step of (c) in cells expressing helper functions; and
   (e) optionally subjecting the lysate from the passaging step to further passaging.

2. The method according to claim 1, wherein the digesting step is performed using a restriction enzyme selected from the group consisting of PmeI, FseI, PacI, PsrI, BcgI, BglI, BsabI, BstXI, DrdI, EcoNI, FseI, and MaMI.

3. The method according to claim 1, wherein the mammalian source is tissue from a non-human primate or human.

4. The method according to claim 1, wherein the cells of step (b) are stably transformed with adenovirus E1a and E1b genes under the control of regulatory control elements which direct expression of the E1a and E1b gene products.

5. The method according to claim 1, wherein the cells of step (b) express AAV helper functions.

6. The method according to claim 1, wherein the cells of step (b) are co-transfected with a vector containing adenoviral sequences consisting of adenovirus E1a, E1b, E2a, E4, a functional fragment of E4 sufficient to provide a helper function for generation AAV virions, and VAI RNA..

7. The method according to claim 1, wherein the cells of step (b) are co-transfected with a vector containing adenoviral sequences consisting of adenovirus E2a, E4, a functional fragment of E4 sufficient to provide a helper function for generation of AAV virions, and VAI RNA.

8. The method according to claim 1, wherein one or more of the at least minimal adenoviral helper functions necessary for packaging and replication of AAV are provided by a non-infectious plasmid.

9. The method according to claim 1, wherein one or more of the at least minimal adenoviral helper functions necessary for packaging and replication of AAV are provided by an infectious plasmid.

10. The method according to claim 1, wherein the at least minimal helper functions necessary for packaging and replication of AAV are provided by one or more adenovirus serotypes.

11. The method according to claim 1, wherein the cell of step (b) is transfected with 0.2 µg to 2 µg of DNA.

12. The method according to claim 1, further comprising the step of transfecting with non-infectious helper adenovirus plasmid and superinfecting the cells with wild-type adenovirus during passaging.

13. The method according to claim 1, further comprising the step of transfecting with non-infectious helper adenovirus plasmid and superinfecting the cells with E1-deleted adenovirus during passaging.

14. The method according to claim 1, wherein the passaging step is performed in 293 cells.

15. The method according to claim 1, wherein the passaging step is repeated twice.

16. A method of detecting adeno-associated viruses (AAV) from cellular DNA in tissues, comprising the step of assaying crude lysate obtained from the method of claim 1 for the presence of AAV.

17. A method of purifying adeno-associated viruses (AAV) from cellular DNA in tissues, comprising the steps of:
   (a) centrifuging crude lysate obtained from the methods of claim 1 to provide a cell pellet; and
   (b) purifying AAV from the cell pellet.

18. The method according to claim 2, wherein the digesting step further comprises the steps of incubating DNA from the sample with PmeI, performing phenol/chloroform extraction, precipitating with ethanol, and dissolving the precipitate.

19. The method according to claim 18, wherein the incubating step is performed for about 12 to 48 hours.

20. The method according to claim 4, wherein the cells are 293 cells.

21. The method according to claim 5, wherein the cells of step (b) express AAV rep proteins.

22. The method according to claim 9, wherein the helper functions are adenovirus E1a and E1b functions provided by a human adenovirus.

23. The method according to claim 10, wherein the adenoviral helper functions are provided by a chimpanzee adenovirus serotype.

24. A method of direct rescue and detection of adeno-associated viruses (AAV) from cellular DNA from tissues comprising the steps of:
- (a) digesting DNA in a sample of genomic DNA from a mammalian tissue source with a restriction enzyme that cleaves the genomic DNA native to the mammalian tissue source without cleaving AAV genomic DNA;
- (b) transfecting the digested DNA into cells;
- (c) incubating the transfected cells;
- (d) superinfecting the transfected cells with adenoviral helper functions so that the cells contain at least the minimal adenoviral functions necessary for packaging and replication of the AAV;
- (e) culturing the superinfected cell under conditions in which the helper functions necessary for replication of AAV are expressed;
- (d) harvesting crude lysate from the superinfected culture; and
- (e) passaging the crude lysate.

25. The method according to claim 24, wherein the harvesting step further comprises subjecting the superinfected cell culture to freeze-thaw to obtain crude lysate.

26. The method according to claim 24, wherein the crude lysate is subjected to two or more passages.

27. A method of direct rescue of adeno-associated viruses (AAV) from cellular DNA from tissues comprising the steps of:
- (a) digesting DNA in a sample of genomic DNA from a mammalian tissue source with a restriction enzyme that cleaves the genomic DNA native to the mammalian tissue source without cleaving AAV genomic DNA;
- (b) co-transfecting the digested DNA and a non-infectious adenoviral helper plasmid comprising adenovirus sequences consisting of the minimal adenoviral functions necessary for packaging and replication of the AAV which are not supplied by the host cell;
- (c) culturing the transfected cells under conditions in which only the minimal adenoviral functions necessary for packaging and replication of the AAV are expressed in the cells;
- (d) treating the cell culture to obtain crude lysate;
- (e) subjecting the crude lysate to a first passage by incubating the crude lysate with cells, thereby permitting infection of AAV into the cells and superinfecting the cells with adenoviral helper functions so that the cells contain at least the minimal adenoviral functions necessary for packaging and replication of the AAV; and
- (f) optionally passaging two or more additional times.

28. A method of direct rescue of adeno-associated viruses (AAV) from cellular DNA from tissues:
- (a) digesting DNA in a sample of genomic DNA from a mammalian tissue source with a restriction enzyme that cleaves the genomic DNA native to the mammalian tissue source without cleaving AAV genomic DNA;
- (b) co-transfecting the digested DNA and an infectious adenoviral helper plasmid comprising the minimal adenoviral functions necessary for packaging and replication of the AAV which are not supplied by the host cell;
- (c) culturing the transfected cells under conditions in which the minimal adenoviral functions necessary for packaging and replication of the AAV are expressed in the cells;
- (d) treating the cell culture to obtain crude lysate; and
- (e) optionally subjecting the crude lysate to two or more passages by incubating the crude lysate with the cells.

29. A kit useful for purifying adeno-associated viruses (AAV) from cellular DNA from tissues according to the method of claim 17 comprising (a) a restriction enzyme that cleaves the genomic DNA native to the host organism without cleaving AAV DNA and (b) cells for infection with AAV in the digested DNA upon incubation with the crude lysate.

* * * * *